(12) United States Patent
Cawthon

(10) Patent No.: US 6,627,178 B1
(45) Date of Patent: Sep. 30, 2003

(54) METHODS, COMPOSITIONS AND SYSTEMS FOR THE PREVENTION AND TREATMENT OF DIAPER RASH

(76) Inventor: Garret D. Cawthon, 105 Highwood Dr., Frankfort, KY (US) 40601

( * ) Notice: Subject to any disclaimer, the term of this patent is extended or adjusted under 35 U.S.C. 154(b) by 0 days.

(21) Appl. No.: 09/364,133

(22) Filed: Jul. 30, 1999

(51) Int. Cl.⁷ .................... A61K 9/00; A61K 33/32; A61K 7/00; A61L 9/04; A01N 59/16
(52) U.S. Cl. ................... 424/45; 424/47; 424/400; 424/401; 424/405; 424/642; 424/725; 424/764; 574/865; 574/886; 574/887
(58) Field of Search ............... 424/401, 78.05, 424/78.07, 642, 45, 400, 47, 405, 725, 764; 514/944, 937, 861, 865, 886, 887

(56) References Cited

U.S. PATENT DOCUMENTS

| | | | |
|---|---|---|---|
| 3,788,521 A | 1/1974 | Laauwe | 222/94 |
| 4,001,391 A | 1/1977 | Feinstone et al. | 424/45 |
| 4,082,222 A | 4/1978 | Boris | 239/331 |
| 4,134,523 A | 1/1979 | Hansen et al. | 222/389 |
| RE30,093 E | 9/1979 | Burger | 222/95 |
| 4,187,985 A | 2/1980 | Goth | 239/337 |
| 4,239,407 A | 12/1980 | Knight | 401/190 |
| 4,389,418 A | 6/1983 | Burton | 424/365 |
| 4,495,168 A | 1/1985 | Schmolka | 424/45 |
| 4,510,734 A | 4/1985 | Banks et al. | 53/449 |
| 4,556,560 A | 12/1985 | Buckingham | 424/145 |
| 4,816,254 A | 3/1989 | Moss | 424/145 |
| 4,857,321 A | 8/1989 | Thomas | 424/95 |
| 4,893,956 A | 1/1990 | Wojcik et al. | 401/130 |
| 4,981,677 A | 1/1991 | Thau | 424/45 |
| 4,996,238 A | 2/1991 | Matravers | 514/865 |
| 4,996,239 A | 2/1991 | Matravers | 514/873 |
| 5,091,193 A | 2/1992 | Enjolras et al. | 424/642 |
| 5,110,593 A | 5/1992 | Benford | 424/401 |
| 5,126,136 A | 6/1992 | Merat et al. | 424/401 |
| 5,194,261 A | 3/1993 | Pichierri | 424/401 |
| 5,223,250 A | 6/1993 | Mitchell et al. | 424/59 |
| 5,229,105 A | 7/1993 | Wilmsmann | 424/59 |
| 5,249,747 A | 10/1993 | Hanson et al. | 239/373 |
| 5,256,403 A | 10/1993 | Gaskin | 424/59 |
| 5,300,286 A | 4/1994 | Gee | 424/78.03 |
| 5,362,488 A | 11/1994 | Sibley et al. | 424/78.05 |
| 5,366,660 A | 11/1994 | Tapley | 252/309 |
| 5,409,903 A | 4/1995 | Polak et al. | 514/23 |
| 5,417,961 A | 5/1995 | Nearn et al. | 424/59 |
| 5,436,007 A | 7/1995 | Hartung et al. | 424/402 |
| 5,441,726 A | 8/1995 | Mitchnick et al. | 424/59 |
| 5,486,631 A | 1/1996 | Mitchnick et al. | 556/10 |
| 5,527,519 A | 6/1996 | Miksits et al. | 423/622 |
| 5,531,985 A | 7/1996 | Mitchell et al. | 424/59 |
| 5,536,492 A | 7/1996 | Mitchnick et al. | 424/59 |
| 5,536,502 A * | 7/1996 | Mulder | 424/405 |
| 5,582,818 A | 12/1996 | Nakanishi et al. | 424/59 |
| 5,587,148 A | 12/1996 | Mitchell et al. | 424/59 |
| 5,609,852 A | 3/1997 | Galley et al. | 424/59 |
| 5,609,854 A | 3/1997 | Guerrero et al. | 424/59 |
| 5,618,529 A | 4/1997 | Pichierri | 424/78.06 |
| 5,639,025 A | 6/1997 | Bush | 239/333 |
| 5,658,956 A | 8/1997 | Martin et al. | 514/724 |
| 5,674,912 A | 10/1997 | Martin | 514/724 |
| 5,721,306 A | 2/1998 | Tsipursky et al. | 524/449 |
| 5,728,391 A | 3/1998 | Ikeya et al. | 424/401 |
| 5,744,469 A | 4/1998 | Tran | 514/220 |
| 5,762,945 A | 6/1998 | Ashley et al. | 424/401 |
| 5,788,389 A | 8/1998 | de Laforcade | 401/190 |
| 5,869,071 A | 2/1999 | Wieselman et al. | 424/401 |
| 5,874,479 A | 2/1999 | Martin | 514/724 |
| 5,876,688 A | 3/1999 | Laundon | 423/622 |
| 5,881,925 A | 3/1999 | Ando | 222/190 |
| 6,423,323 B2 * | 7/2002 | Neubourg | 424/401 |

* cited by examiner

*Primary Examiner*—Jose' G. Dees
*Assistant Examiner*—Marina Lamm
(74) *Attorney, Agent, or Firm*—Woodard, Emhardt, Moriarty, McNett & Henry LLP

(57) ABSTRACT

Provided by the invention are systems for applying diaper rash treatment compositions to a selected skin treatment area without the need for the person administering the treatment to directly contact the composition or the skin of the patient. Application of the diaper rash treatment composition is accomplished by forming the composition into a mist or spray using an atomizing spray dispenser.

30 Claims, 6 Drawing Sheets

METHODS, COMPOSITIONS AND SYSTEMS FOR THE PREVENTION AND TREATMENT OF DIAPER RASH

BACKGROUND

1. Field of the Invention

The present invention relates to methods, compositions and systems for the prevention and treatment of diaper rash.

2. Discussion of Related Art

Diaper rash (also referred to as diaper dermatitis or incontinent dermatitis) is a common form of irritation and inflammation affecting both infants and incontinent adults, typically in those areas normally covered by a diaper or in areas immediately adjacent to the diaper area. It is generally accepted that diaper rash is a condition that is, in its most simple stages, a contact irritant dermatitis. The irritation of simple diaper rash results from extended contact of the skin with urine, or feces, or both. Diapers are worn to catch and hold the body waste, but generally hold the waste in direct contact with the skin until changed, sometimes for extended periods of time. The same is true for an incontinence pad, or incontinence brief.

While it is known that body waste causes diaper rash, identification of the precise component or components of the urine and/or feces which are responsible for the resulting irritation of the skin remains the subject of much controversy. The most commonly accepted list of factors linked to diaper rash includes ammonia, bacteria, the products of bacteria action, urine pH, *Candida albicans*, and moisture.

Encompassed by the term "diaper rash" are a wide variety of related conditions including, for example, friction rash, irritant rash, allergic rash, intertrigo, seborrhea rash and psoriasis. Friction rash is the most common form of diaper rash, and affects almost all infants at some time. It is most common on areas where friction is most pronounced, such as the inner thighs, or under the elastic of diapers that are too tight. It comes and goes quickly, and responds well to frequent diaper changes, airing out, and protective barriers. Irritant rash is usually most conspicuous on the exposed areas, such as the round part of the buttocks. It tends to spare skin folds and creases, and is generally the result of contact with stool enzymes or irritants such as harsh soaps, baby wipes, detergents or topical medicines. Allergic rash may occur in combination with an irritant rash or by itself. It is also more common on exposed areas, and the rash resembles poison oak. Intertrigo is caused by moist heat, such as that commonly occurs deep in skin folds. The involved skin looks thin, as if it has lost several layers. Seborrhea rash is a salmon-colored, greasy rash with yellowish scales, and is also typically worse in skin folds. Psoriasis is a stubborn rash that does not necessarily look distinctive. Other signs of psoriasis usually accompany the diaper rash, though, such as pitting of the nails or dark red areas with sharp borders and fine silvery scales on the trunk, face, or scalp. In addition to its common appearance in the diaper area, the term diaper rash is also intended to refer to skin irritations at other areas of the human body that may be caused by prolonged exposure to, for example, moisture, heat, irritants, enzymes and/or pressure.

Skin wetness appears to be the common denominator underlying the various causes of diaper rash. Urinary wetness increases skin friction, raises the skin pH, makes the skin less cohesive, and makes it more permeable. These effects combine to intensify the action of stool enzymes or other irritants that then inflame the skin. Even skin lesions of systemic illnesses tend to concentrate in areas where the skin is already damaged. In a typical diaper rash, with the protective layer of the outermost layer of skin (the stratum corneum) damaged, microorganisms such as yeast or bacteria can more readily invade the inflamed skin.

Because the suspected agents of diaper rash, discussed above, all possess diverse properties and require varied therapies, conventional methods of treatment for diaper dermatitis have been directed toward a straightforward attempt to minimize the contact of the skin with the feces or urine present in a soiled diaper. An artificial barrier is usually provided between the skin and the body waste to accomplish this. There have also been attempts directed toward counteracting other suspected causes of diaper rash by promoting dryness in the diapered area, and preventing microbial growth and inflammation with conventional agents. Such a strategy would include frequent diaper changing, reduced use of plastic pants, triple diapering, careful washing and sterilization of diapers, treatment with an anti-Candidal agent, reduction of inflammation (by topical application of a low potency glucocorticoid steroid), and the possible use of a bacteriostatic agent as a prophylactic measure in the perineal rinse. However, because the exact components of urine or feces which act as factors or cofactors contributing to diaper dermatitis have never been precisely identified, the most effective method of treating diaper rash to date has been the artificial barrier. This has led to the frequent use of an occlusive, barrier-type topical, such as petrolatum or zinc oxide, to provide protection, preventing the unknown offending component from coming in contact with the skin.

Presently, there are a wide variety of ointments, creams or lotions known and available in the market for the treatment of diaper rash. Most of these products include ingredients that offer some beneficial property to the product, for example, by acting as a water repellant, emollient, neutralizer or antibiotic. Examples of ingredients that are commonly included in such ointments are mineral oil, silicone fluids (e.g. dimethicone and cyclomethicone), petrolatum, cod liver oil, lanolin, zinc oxide, talc, calamine, kaolin, topical starch and allantoin. For example, Desitin® ointment (Pfizer, Inc.) is probably the most common topical used in treating diaper rash. It contains common barrier materials (zinc oxide and petrolatum) and additionally contains two common skin conditioning agents (cod liver oil and lanolin).

Examples of patents that describe various diaper rash treatment compositions include the following: U.S. Pat. No. 5,110,593 to Benford, U.S. Pat. No. 5,300,286 to Gee, U.S. Pat. No. 5,436,007 to Hartung et al., U.S. Pat. No. 5,744,469 to Tran, U.S. Pat. No. 4,857,321 to Thomas, U.S. Pat. No. 5,229,105 to Wilmsmann, U.S. Pat. No. 5,091,193 to Enjolras et al., U.S. Pat. No. 5,869,071 to Wieselman et al., U.S. Pat. No. 5,194,261 to Pichierri, U.S. Pat. No. 5,362,488 to Sibley et al. and U.S. Pat. No. 5,762,945 to Ashley et al. These, and all other references cited herein are hereby incorporated by reference herein in their entireties.

Many recent developments in the field of diaper rash treatment have focused on new ingredients that offer either antibiotic performance or act as a superior moisture barrier. For example, there are a number of pharmaceutical actives that can be used, but these are not available in over-the-counter products. Additionally, there have been proposed lotions having reactive polymeric components that form a plastic coating on the surface of the skin. Examples of such developments include U.S. Pat. No. 5,879,688 to Coury et al., U.S. Pat. No. 5,874,479 to Martin, U.S. Pat. No. 5,762,945 to Ashley, U.S. Pat. No. 5,728,391 to Ikeya et al., U.S. Pat. No. 5,721,306 to Tsipursky et al., U.S. Pat. No. 5,674, 912 to Martin, U.S. Pat. No. 5,658,956 to Martin et al., and U.S. Pat. No. 5,618,529 to Pichierri.

A major drawback of most products currently available for the treatment of diaper rash, however, is that they are very viscous and messy to administer to the skin. Such products require that the person applying the product spread the product by rubbing the same into or over the skin. While this requirement is typically acceptable in the case of a parent applying the product to the skin of an infant child, it is a drawback where a caregiver is in charge of providing such a treatment to multiple persons, especially multiple incontinent adults. The application of the product is messy and awkward because the product is difficult to wash off of ones hand due to its oily, hydrophobic nature. Additionally, the caregiver must first use one set of gloves to clean the patient, and then use another set of gloves to apply the ointment or lotion. This results in wasted time and resources.

Other new products address the difficulty and mess associated with applying viscous ointments and lotions by providing systems that have pads or other applicators that can be used to smear the ointment onto the skin. A representative example of such a system is set forth in U.S. Pat. No. 4,893,956 to Wojcik et al. A disadvantage of such applicators, however, is that they may become contaminated upon use and should therefore be discarded after a single use.

The above shortcomings of the prior art are addressed by the present invention, which provides methods, compositions and systems for administering diaper rash compositions to a selected skin treatment area without the mess, inconvenience and inefficiency experienced in the prior art.

SUMMARY OF THE INVENTION

The present invention addresses a number of problems associated with currently-known diaper rash treatments by providing methods, compositions and systems for diaper rash treatment involving application of a treatment composition as an atomized spray. Provided by the invention are systems for applying a variety of diaper rash treatment compositions to a selected treatment area without the need for the person administering the treatment to directly contact the composition or the skin of the patient.

In one aspect of the invention, there is provided a method for treating diaper rash, the method comprising (1) providing a diaper rash treatment system comprising an atomizing spray dispenser and a diaper rash treatment composition; wherein the composition has a viscosity of from about 1 to about 1000 centipoise; wherein the dispenser comprises a container and an atomizing spray delivery mechanism affixed to the container; and wherein the composition is positioned in the container, (2) selecting a skin treatment area featuring incontinent dermatitis or substantially at risk of developing incontinent dermatitis; and (3) passing the composition through the mechanism to atomize the composition and to propel the atomized composition toward the skin treatment area; wherein the composition comprises at least about 1 percent solid particulate material by weight and at least about 20 percent by weight of a fluid base material. The solid material is preferably particulate zinc oxide.

In another aspect of the invention, there is provided a method for treating diaper rash, the method comprising (1) providing a diaper rash treatment system comprising an atomizing spray dispenser and a diaper rash treatment composition; wherein the composition has a viscosity of from about 1 to about 1000 centipoise; wherein the dispenser comprises a container and an atomizing spray delivery mechanism affixed to the container; and wherein the composition is positioned in the container; (2) selecting a skin treatment area featuring incontinent dermatitis or substantially at risk of developing incontinent dermatitis; and (3) passing the composition through the mechanism to atomize the composition and to propel the atomized composition toward the skin treatment area; wherein the composition comprises lanolin, petrolatum, cod liver oil and a fluid base material.

In another aspect of the invention, there is provided a method for treating diaper rash, the method comprising (1) providing a diaper rash treatment system comprising an atomizing spray dispenser and a diaper rash treatment composition; wherein the composition has a viscosity of from about 1 to about 1000 centipoise; wherein the dispenser comprises a container and an atomizing spray delivery mechanism affixed to the container; and wherein the composition is positioned in the container; (2) selecting a skin treatment area featuring incontinent dermatitis or substantially at risk of developing incontinent dermatitis; and (3) passing the composition through the mechanism to atomize the composition and to propel the atomized composition toward the skin treatment area; wherein the composition comprises a member selected from the group consisting of calendula, chamomile and comfrey.

The invention provides in another aspect a system for treating diaper rash, the system comprising (1) a diaper rash treatment composition having a viscosity of from about 1 to about 1000 centipoise, wherein the composition comprises at least about 1 percent particulate zinc oxide by weight and at least about 20 percent by weight of a fluid base material; and (2) an atomizing spray dispenser for delivering the composition to a skin treatment area; wherein the dispenser comprises a container and an atomizing spray delivery mechanism affixed to the container; and wherein the composition is positioned in the container.

The invention provides in another aspect a system for treating diaper rash, the system comprising (1) a diaper rash treatment composition having a viscosity of from about 1 to about 1000 centipoise, wherein the composition comprises lanolin, petrolatum, cod liver oil and a fluid base material; and (2) an atomizing spray dispenser for delivering the composition to a skin treatment area; wherein the dispenser comprises a container and an atomizing spray delivery mechanism affixed to the container; and wherein the composition is positioned in the container.

The invention provides in another aspect a system for treating diaper rash, the system comprising (1) a diaper rash treatment composition having a viscosity of from about 1 to about 1000 centipoise, wherein the composition comprises a member selected from the group consisting of calendula, chamomile and comfrey and a fluid base material; and (2) an atomizing spray dispenser for delivering the composition to a skin treatment area; wherein the dispenser comprises a container and an atomizing spray delivery mechanism affixed to the container; and wherein the composition is positioned in the container.

In another aspect of the invention, there is provided a method for treating diaper rash, comprising (1) selecting a substantially clean skin treatment area afflicted by incontinent dermatitis or substantially at risk of developing incontinent dermatitis; and (2) propelling toward the skin treatment area an atomized spray comprising a diaper rash treatment composition having a viscosity of from about 1 to about 1000 centipoise.

It is an object of the invention to provide novel methods, compositions and systems for preventing or treating diaper rash.

It is another object of the invention to provide novel methods, compositions and systems for preventing or treating diaper rash whereby a treatment composition may be administered to a skin surface without the need for the person administering the composition to come into contact with the composition or the skin of the patient.

An additional object of the invention is to provide novel methods, compositions and systems for preventing or treating diaper rash whereby a treatment composition may be administered to a skin surface by atomizing the composition and propelling the atomized composition toward the skin surface.

Further objects, advantages and features of the present invention will be apparent from the detailed description herein.

BRIEF DESCRIPTION OF THE DRAWINGS

Although the characteristic features of this invention will be particularly pointed out in the claims, the invention itself, and the manner in which it may be made and used, may be better understood by referring to the following description taken in connection with the accompanying figures forming a part hereof.

DETAILED DESCRIPTION OF THE PREFERRED EMBODIMENTS

For purposes of promoting an understanding of the principles of the invention, reference will now be made to particular embodiments of the invention and specific language will be used to describe the same. It will nevertheless be understood that no limitation of the scope of the invention is thereby intended, such alterations and further modifications in the invention, and such further applications of the principles of the invention as described herein being contemplated as would normally occur to one skilled in the art to which the invention pertains.

Figure 1:
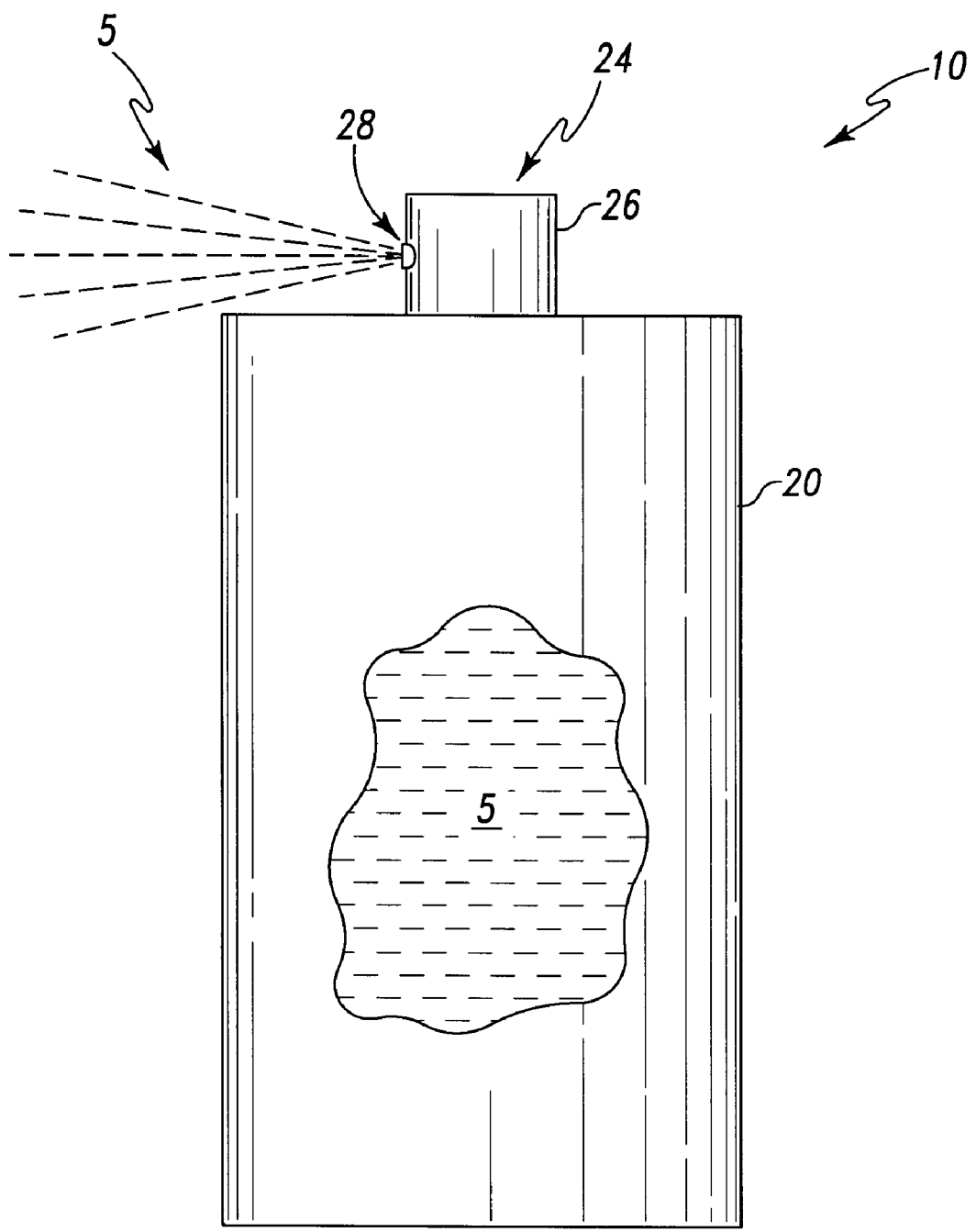
FIG. 1 is a side elevational view, with a cut-out portion, of an atomizing spray dispenser in accordance with one embodiment of the invention.

Referring to FIG. 1, to practice the invention, a diaper rash treatment composition 5 is placed into an atomizing spray dispenser 10. The dispenser is preferably a container 20 equipped with a spray delivery mechanism 24 configured to atomize and propel the composition toward a treatment surface. Compositions described herein exhibit excellent features for the treatment of diaper rash. When a proper amount of the composition is atomized and propelled by a suitable atomizing spray delivery mechanism, the composition forms a buttery layer, or coating, over the surface, thereby providing a barrier to moisture, and a soothing finction to the skin.

It is preferred that the composition have a suitably low viscosity that it may be readily converted to an atomized spray, but that the viscosity not be too low because a viscosity that is too low may result in the composition running off of the treatment surface. In this regard, the composition preferably has a viscosity of from about 1 to about 1000 centipoise. More preferably, the viscosity of the composition is from about 20 to about 650 centipoise, more preferably from about 100 to about 600 centipoise, and most preferably from about 400 to about 500 centipoise. The composition may comprise a liquid, a combination of liquids or a combination of one or more liquids and one or more solids that features a suitable viscosity. While a variety of additional ingredients may be included in an inventive composition, as discussed more fully below, an important ingredient in an inventive composition is a fluid base material.

The term "fluid base material" is used herein to refer to a fluid into which additional ingredients may be mixed, dissolved and/or suspended. The fluid base material selected is preferably an oil having a viscosity of from about 1 centipoise to about 1000 centipoise. Excellent oils that may be used are mineral oils, silicone oils, plant-based oils or mixtures thereof. The term "mineral oil" is used herein to refer to a liquid petroleum derivative. Examples of excellent, commercially available mineral oils that may be used in accordance with the invention include Witco Corporation's CARNATION® Mineral Oil (viscosity range of 9–12 centipoise) or Penreco Corporation's DRAKEOL® Mineral Oil (Drakeol 7 having a viscosity of 9–11 centipoise).

The term "silicone oil" is used herein to refer to a liquid silicone composition. Excellent silicone oils that may be used, for example, are cyclomethicone, dimethicone and derivatives thereof, and commercially available silicone oils include Dow Corning Corporation's 200 polydimethylsiloxane fluids and GE Silicones' SF series of low viscosity Dimethyl fluids. Cyclomethicone is a volatile compound, and is advantageously included in certain inventive compositions because it evaporates when applied to the skin's surface, making the coating more dry to the touch. Other volatile compounds may also be used in this way, including, for example, an organic solvent such as isododecane. Such compounds are particularly useful in embodiments of the invention that utilize an aerosol dispenser as the delivery mechanism, as described in more detail below, because the volatile compounds may be used as liquid solvents in the container that evaporate when dispensed from the container to leave a drier coating on the skin surface.

The term "plant-based oil" is used herein to refer to a non-petroleum biomass derived oil, such as a vegetable or fruit oil, including, for example, almond oil, peanut oil, wheat germ oil, linseed oil, jojoba oil, apricot pit oil, walnut oil, palm nut oil, pistachio nut oil, sesame seed oil, rapeseed oil, cade oil, corn oil, peach pit oil, poppyseed oil, pine oil, castor oil, soybean oil, avocado oil, safflower oil, coconut oil, hazelnut oil, olive oil, grape seed oil, sunflower oil, apricot kernal oil, geranium oil, ricebran oil and mixtures thereof. It is of course not intended that the fluid base material be limited to the above exemplary compositions. As an alternative to plant-based oil, silicone oil and mineral oil, another material that may excellently be used as the fluid base material, or included therein, is cod liver oil.

The fluid base material may alternatively be water, an oil-in-water emulsion or a water-in-oil emulsion. Inventive compositions including water or an emulsion as the base material are often considered to be more elegant because such compositions have a less greasy feel. Such compositions are also typically less expensive to make because in most places water is readily available and inexpensive. Additional advantages of having water in an inventive composition are that the water provides a source of moisture for dry skin, and that the presence of water allows the inclusion of additional water-loving ingredients that would not become suitably dissolved or dispersed in an oil-based composition. When water is included in an inventive composition that also comprises one or more oils, it is readily understood that an emulsifying agent will typically be necessary to produce a stable mix of the water and non-aqueous ingredients in the composition. Examples of suitable emulsifiers that may be used include cetyl alcohol, stearyl alcohol, cetearyl alcohol and glycerol monolaurate. It is of course not intended that this list be limiting but simply provide examples of emulsifiers that may be used in accordance of the invention. Additional suitable emulsifiers are set forth on pages 90 to 94 of the C.T.F.A. Cosmetic Ingredient Handbook, First Edition, 1988, which is hereby incorporated by reference. Further guidance to the preparation of stable emulsions generally may be found in U.S. Pat. No. 5,417,961 to Nearn et al., which is hereby incorporated herein by reference in its entirety.

In one excellent aspect of the invention, the composition comprises at least about 1 percent solid particulate material by weight and at least about 20 percent by weight of a fluid base material. In this aspect of the invention, the solid particulate material is preferably particulate zinc oxide. The zinc oxide preferably has an average particle size of from about 0.01 microns to about 100 microns, more preferably from about 0.01 microns to about 10 microns and most preferably from about 0.01 microns to about 1 micron.

Zinc oxide particles of from about 0.01 microns to about 0.1 microns are commonly referred to as microfine zinc oxide particles. A feature of microfine zinc oxide that is desirable in some applications is that the microfine zinc oxide is translucent when dispersed in a conventional fluid base material. Inventive formulations including microfine zinc oxide therefore do not have the characteristic opaque white appearance of formulations including zinc oxide having larger particle sizes. It is also believed that microfine zinc oxide provides additional advantages over larger particulates, including a smoother film coating on the skin, lower viscosity at the same overall zinc oxide loading, better penetration of the zinc oxide into the skin's cracks and crevices, more even coverage with the finer particles, and higher surface area providing for more reaction/therapeutic activity.

It is also intended that the term "zinc oxide" encompass coated zinc oxide. A typical coating is silicone-based and is used to help disperse the zinc oxide in solution and to lower the viscosity of a zinc oxide mixture. It has been reported that uncoated zinc oxide particles swell in certain solvents, such as, for example, octyl palmitate. An advantage of coating in certain embodiments of the invention is that silicone coated zinc oxide particles are hydrophobic, non-reactive and not affected by water. Coated hydrophobized zinc oxides or particles also have a significantly decreased photoreactivity, which makes them more resistant to degradation and more chemically inert than non-coated zinc oxides. Hydrophobized zinc oxide is therefore particularly useful in compositions that are applied to skin that is exposed to sunlight or other ultraviolet radiation The ratio of zinc oxide to fluid base material in this composition is preferably selected such that the composition has a suitable viscosity at a given temperature as described above. It is readily understood that the ratio selected is dependent upon the desired viscosity for a given system. For example, different delivery systems may function optimally when used to deliver compositions having different overall viscosities. Further, the preferred ratio also depends upon the viscosity of the fluid base material selected for use and upon the particle size distribution of the zinc oxide. These and other factors may be readily determined and considered by a person of ordinary skill in the art, without undue experimentation, to make an inventive composition having a suitable viscosity. The composition in this aspect of the invention preferably comprises from about 1 to about 40 percent zinc oxide by weight, more preferably from about 5 to about 25 percent and, most preferably, from about 10 to about 15 percent. The composition also preferably comprises from about 20 to about 99 percent fluid base material by weight, more preferably from about 33 to about 80 percent and, most preferably from about 55 to about 75 percent.

The composition may also optionally include one or more of a wide variety of beneficial additives that may be incorporated to provide additional soothing and/or healing to the skin and/or for other reasons. For example, the composition may comprise lanolin to improve the skin conditioning quality of the composition. It is understood that the term "lanolin" refers to the various forms of lanolin-and its derivatives, including, for example, lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate, lanolin alcohols ricinoleate, acetate of lanolin alcohols, ricinoleate, acetate of ethoxylated alcohols-esters, hydrogenolysis of lanolin, ethoxylated hydrogenated lanolin and ethoxylated sorbitol lanolin. Another excellent skin conditioning composition that may be included, if not already included in the fluid base material, is cod liver oil. The composition may also desirably include paraffin, microcrystalline wax and/or petrolatum to provide an excellent moisture barrier material. Additional ingredients that may optionally be included in an inventive composition are fragrances, dyes, preservatives, anti-bacterial agents, anti-fungal agents and emollients. It is of course not intended that this list limit the invention, but simply provide examples of ingredients that might be included in inventive compositions. In addition, the composition may comprise one or more different solids as an alternative to zinc oxide or in addition to zinc oxide, such as, for example, talc, calamine or kaolin.

When including one or more beneficial additives, it is important to consider the effect that the one or more additives have on the overall viscosity of the composition. Thus, adjustments of the zinc oxide to fluid base material ratio may be necessary to achieve a desired viscosity when including one or more beneficial additives to achieve a desired combination of additional features.

In this aspect of the invention, the composition may also preferably include from about 0 to about 16 percent lanolin by weight, more preferably from about 5 to about 15 percent and, most preferably from about 5 to about 10 percent; from about 0 to about 25 percent petrolatum by weight, more preferably from about 5 to about 15 percent and, most preferably from about 5 to about 10 percent; and from about 0 to about 12 percent cod liver oil by weight, more preferably from about 5 to about 12 percent and, most preferably from about 5 to about 10 percent.

An excellent composition in the practice of the invention comprises from about 1 to about 40 percent zinc oxide, from about 20 to about 99 percent fluid base material, from about 0 to about 16 percent lanolin, from about 0 to about 12 percent cod liver oil and from about 0 to about 25 percent petrolatum, all by weight. In one preferred embodiment, the fluid base material comprises from about 20 to about 100 percent mineral oil and from about 0 to about 20 percent silicone oil by weight. Alternatively, the fluid base material may comprise from about 20 to about 100 percent silicone oil and from about 0 to about 20 percent mineral oil by weight.

Another preferred composition comprises from about 5 to about 25 percent zinc oxide, from about 33 to about 80 percent fluid base material, from about 5 to about 15 percent lanolin, from about 5 to about 12 percent cod liver oil and from about 5 to about 15 percent petrolatum, all by weight. An additional preferred composition comprises from about 10 to about 15 percent zinc oxide, from about 55 to about 75 percent fluid base material, from about 5 to about 10 percent lanolin, from about 5 to about 10 percent cod liver oil and from about 5 to about 10 percent petrolatum, all by weight. The composition may also advantageously include from about 5 to about 10 percent talc and/or microcrystalline wax to increase the viscosity of the composition.

A composition that has been found to have particularly excellent features in accordance with the invention comprises about 25 percent zinc oxide, about 5 percent lanolin, about 5 percent petrolatum, about 5 percent microcrystalline wax, about 10 percent cod liver oil, about 40 percent mineral oil and about 10 percent cyclomethicone, all by weight.

In an alternate aspect of the invention, there is provided a diaper rash treatment composition that comprises a fluid base material and a source of vitamin A (also referred to as "retinol") and vitamin D (also referred to as "cholecalciferol"). An excellent source of vitamins A and D in this aspect of the invention is cod liver oil; however, it is understood that alternate sources may be used as alternatives, or in addition to, cod liver oil. For example, the vitamin source may comprise purified vitamin A, purified vitamin D and/or vitamin A palmitate. The composition preferably comprises lanolin, petrolatum, cod liver oil and a fluid base material (which may also include cod liver oil). An excellent composition, for example, comprises from about 1 to about 16 percent lanolin, from about 47 to about 97 percent fluid base material, from about 1 to about 12 percent cod liver oil and from about 1 to about 25 percent petrolatum, all by weight. Another preferred composition comprises from about 5 to about 16 percent lanolin, from about 57 to about 85 percent fluid base material, from about 5 to about 12 percent cod liver oil and from about 5 to about 15 percent petrolatum, all by weight. An additional preferred composition comprises from about 10 to about 16 percent lanolin, from about 57 to about 70 percent fluid base material, from about 10 to about 12 percent cod liver oil and from about 10 to about 15 percent petrolatum, all by weight. It is understood that, where the fluid base material wholly or partially comprises cod liver oil, the cod liver oil is intended to satisfy the recitation of the cod liver oil and the fluid base material.

A composition that has been found to have particularly excellent features in accordance with the invention comprises about 10 percent cod liver oil, about 10 percent lanolin, about 10 percent petrolatum, about 8 percent microcrystalline wax, about 47 percent mineral oil, and about 15 percent cyclomethicone, all by weight.

In another excellent aspect of the invention, there is provided a diaper rash treatment composition that is made using natural ingredients. The composition preferably comprises a fluid base material and a solid particulate material or an herbal extract selected from the group consisting of calendula, chamomile, comfrey and mixtures thereof. The fluid base material in this aspect of the invention is preferably a plant-based oil, a silicone oil, water or a mixture thereof. For example, plant-based oils that may be advantageously selected include almond oil, peanut oil, wheat germ oil, linseed oil, jojoba oil, apricot pit oil, walnut oil, palm nut oil, pistachio nut oil, sesame seed oil, rapeseed oil, cade oil, corn oil, peach pit oil, poppyseed oil, pine oil, castor oil, soybean oil, avocado oil, safflower oil, coconut oil, hazelnut oil, olive oil, grape seed oil, sunflower oil, apricot kernal oil, geranium oil, ricebran oil and mixtures thereof. Beneficial additives that may be included in this aspect of the invention include, for example, lanolin, cod liver oil, microcrystalline wax, bees wax and derivatives thereof. Derivatives of bees wax may include, for example, bees wax with ethoxylated sorbitol of varying ethylene oxide content and dimethicone copolyol beeswax.

An excellent composition for use in accordance with this aspect of the invention comprises from about 1 to about 15 percent of a member selected from the group consisting of calendula extract, chamomile extract, comfrey extract and mixtures thereof, from about 50 to about 99 percent fluid base material, from about 0 to about 15 percent lanolin, and from about 0 to about 20 percent bees wax, all by weight. The extracts are preferably "(4:1)" extracts, wherein the designation "(4:1)" is used to identify the weight ratio of solvent to herb used to make the extract using extraction methods known in the art. It is of course not intended that the invention be limited by the manner in which such an extract is prepared, it being understood that a wide variety of ratios, and a wide variety of extracts, may be used.

Another preferred composition comprises from about 1 to about 9 percent of a member selected from the group consisting of calendula extract, chamomile extract, comfrey extract and mixtures thereof, from about 67 to about 99 percent fluid base material, from about 0 to about 12 percent lanolin, and from about 0 to about 12 percent bees wax, all by weight. An additional preferred composition comprises from about 3 to about 9 percent of a member selected from the group consisting of calendula extract, chamomile extract, comfrey extract and mixtures thereof, from about 81 to about 99 percent fluid base material, from about 0 to about 5 percent lanolin, and from about 0 to about 5 percent bees wax, all by weight.

A composition that has been found to have particularly excellent features in accordance with the invention comprises about 3 percent calendula extract, about 3 percent chamomile extract, about 3 percent comfrey extract, about 5 percent lanolin, about 5 percent beeswax, about 1 percent lavender oil, about 1 percent geranium oil, about 54 percent sunflower seed oil and about 25 percent cyclomethicone, all by weight.

As mentioned above, other additives may be included in inventive compositions, including conventional additives typically employed in skin care compositions. For example, fragrance oils may be used to mask the odor of other ingredients and/or for cosmetic appeal. Dyes may also be used to color the composition. In addition, preservatives, such as, for example, DMDM Hydantoin, methylparaben or other esters of parahydroxy benzoic acid, and the ester of propylparahydroxy benzoic acid and benzethonium chloride may be used. Other emollients such as aloe vera and vitamins A, D and E may also be used. Emulsion compositions made in accordance with the invention can also optionally include additional active ingredients such as antimicrobial agents, antibacterial agents and antifungal agents.

An inventive composition may be made by mixing the ingredients and heating the mixture to an elevated temperature below the decomposition temperature of the ingredients. Heating is preferred to ensure that solid ingredients are melted, dissolved and/or dispersed in the composition and to more efficiently and stably achieve an acceptable degree of mixing. The mixture is preferably heated to a temperature in a range of from about 40° C. to about 75° C. When temperature sensitive ingredients, such as, for example, herbal ingredients and cod liver oil, are included in an inventive composition, these ingredients should be added after the mixture's temperature has been lowered to below about 40° C. When cod liver oil is used as the fluid base material, it is understood that the mixing should be conducted at a temperature below the decomposition temperature of the cod liver oil. A high shear mixer, such as a triple roll mixer or Charles Ross & Son Company's high-speed mixer-emulsifier, may advantageously be used to assist in the development of a uniform, stable composition.

Referring to FIG. 1, a composition made or selected in accordance with the invention is preferably applied to a skin treatment surface by atomizing the composition 5 and propelling the atomized composition toward the surface using a suitable atomizing spray dispenser 10 comprising a container 20 and an atomizing spray delivery mechanism 24. The atomizing spray delivery mechanism 24 preferably releases the composition 5 from the container 20 through an outlet port 28 when a valve is mechanically actuated. The mechanism 24 preferably features a reciprocating actuator 26.

Figure 2:
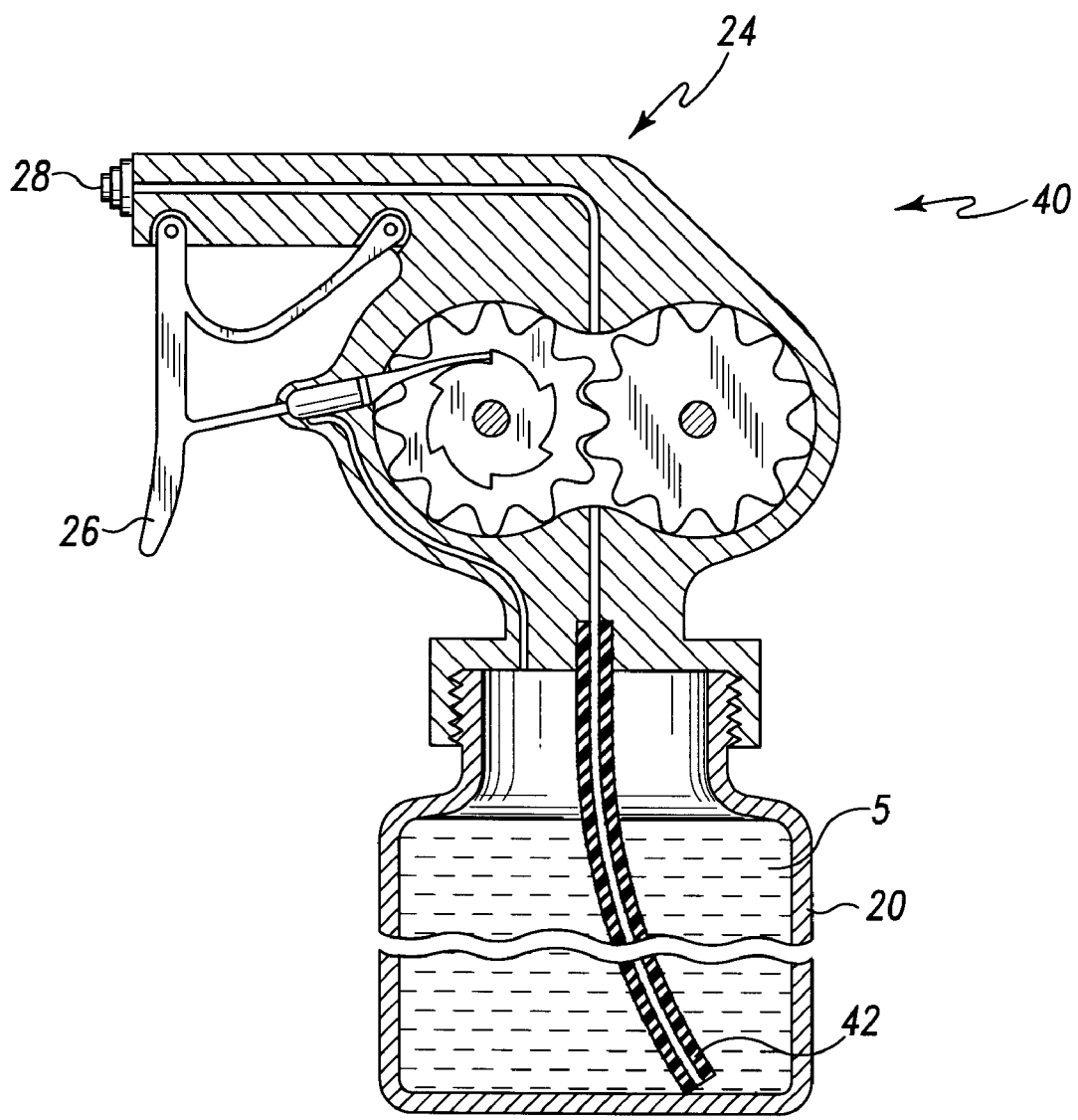
FIG. 2 is a sectional side elevational view of a representative atomizing pump spray dispenser in accordance with another embodiment of the invention.

An excellent atomizing spray delivery mechanism that may be used in accordance with the invention is an atomizing pump spray dispenser 40, a representative example of which is depicted in FIG. 2. As used herein, the term "atomizing pump spray dispenser" is intended to refer to a device that, upon activation of a mechanical pump, such as gear pump 43 of FIG. 2, draws a composition 5 from a container 20, atomizes the composition, and propels the atomized composition substantially in a predetermined direction. It is understood that the composition 5 drawn from container 20 preferably enters a conduit in fluid communication with the pump and having an inlet port 42 positioned near the bottom of container 20. "Atomizing" a composition refers to the separation of the composition into relatively small unitary masses (i.e., typically on the order of about 1 to about 100 microns).

It is important to recognize that the term "pump dispenser" has been used in the prior art to refer to devices for drawing a cream, lotion or ointment from a container and propelling a stream of the cream, lotion or ointment, such as, into the palm of ones hand. This type of dispenser is distinguished from an "atomizing pump spray dispenser" as described herein, because a pump dispenser for propelling a stream of a cream, lotion or ointment is incapable of atomizing the cream, lotion or ointment into an atomized mist or spray. It is understood that the unitary masses, when propelled from an atomizing pump spray dispenser, form a mist or a spray. When the atomized composition is directed toward a given surface at a suitable velocity, the unitary masses adhere to the surface to provide a thin, often buttery, coating of the composition on the surface.

A wide variety of atomizing pump spray dispensers are commercially available, as are a wide variety of designs for actuating the dispensers and for atomizing the composition. While it is not intended that the invention be limited by the design of the atomizing pump spray dispensers, representative examples are set forth in U.S. Pat. No. 5,639,025 to Bush, U.S. Pat. No. 5,881,925 to Ando and U.S. Pat. No. 5,249,747 to Hanson et al.

Another excellent atomizing spray dispenser that may be used in accordance with the invention is a pressure release device. As used herein, the term "pressure release device" is intended to refer to a device that contains a composition under pressure, and, when actuated, opens a valve to release the composition from the pressurized compartment, atomizes the composition, and propels the atomized composition substantially in a predetermined direction by using energy provided by the force of the pressure. The composition may advantageously be maintained under pressure by placing the composition in a pressurized compartment of the container. The composition is releasably contained in the pressurized compartment and when a manually actuating valve is opened, the composition is released from the compartment, atomized, and released from the device as an atomized spray.

Figure 3:
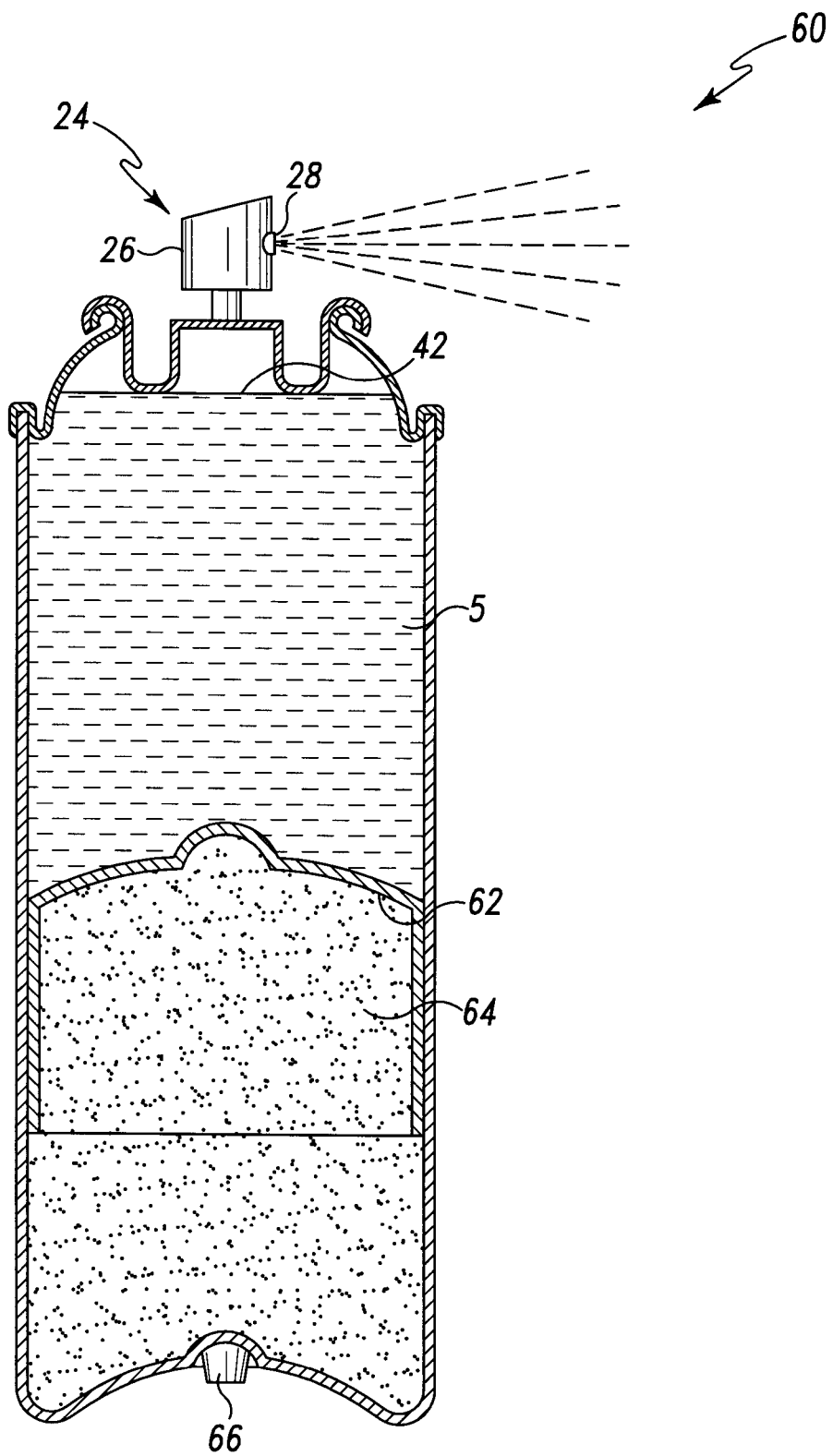
FIG. 3 is a sectional side elevational view of a representative piston-style dispenser in accordance with another embodiment of the invention.
Figure 4:
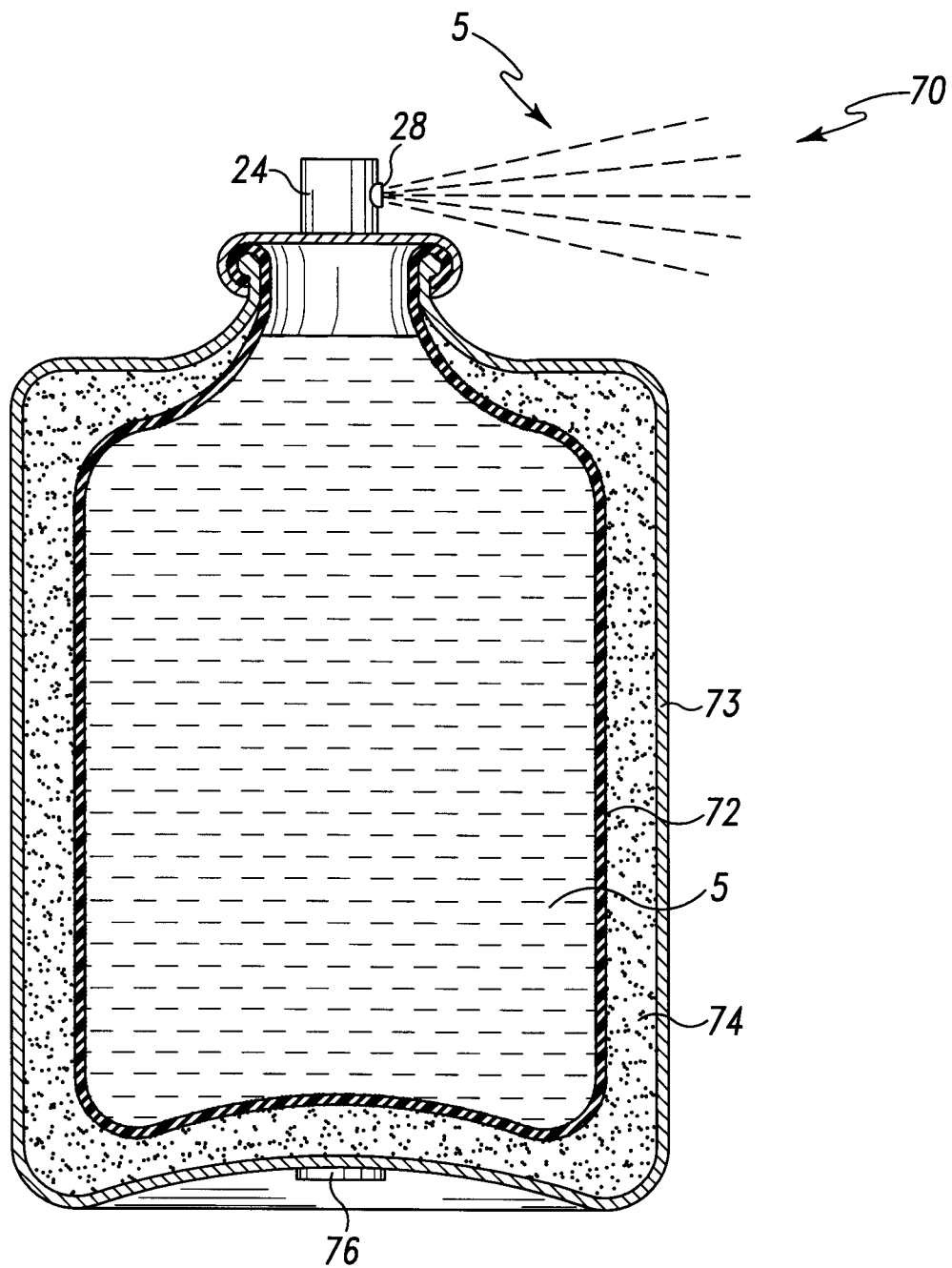
FIG. 4 is a sectional side elevational view of a representative bag-in-can style dispenser in accordance with another embodiment of the invention.
Figure 5:
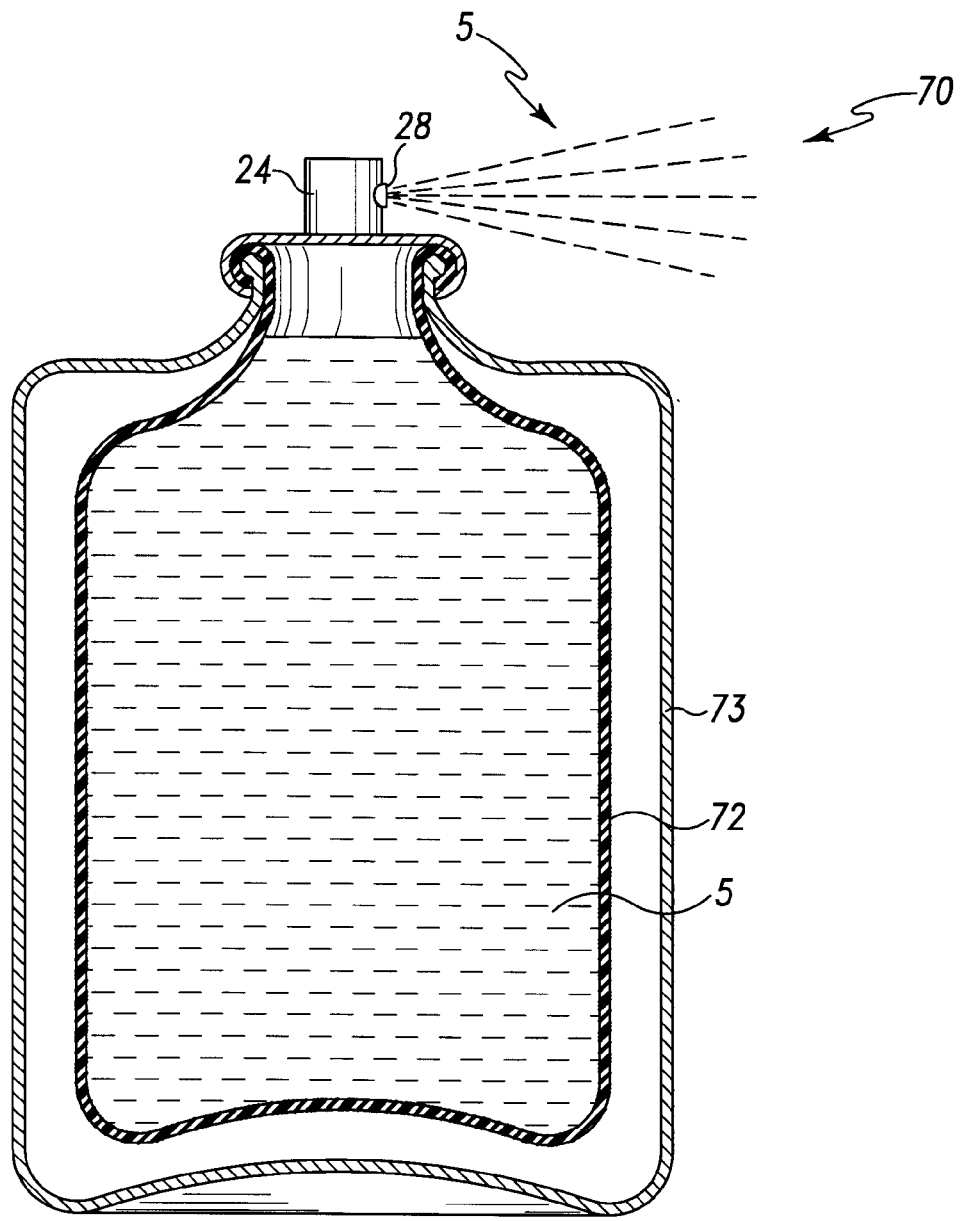
FIG. 5 is a sectional side elevational view of a representative bag-in-can style dispenser in accordance with another embodiment of the invention.
Figure 6:
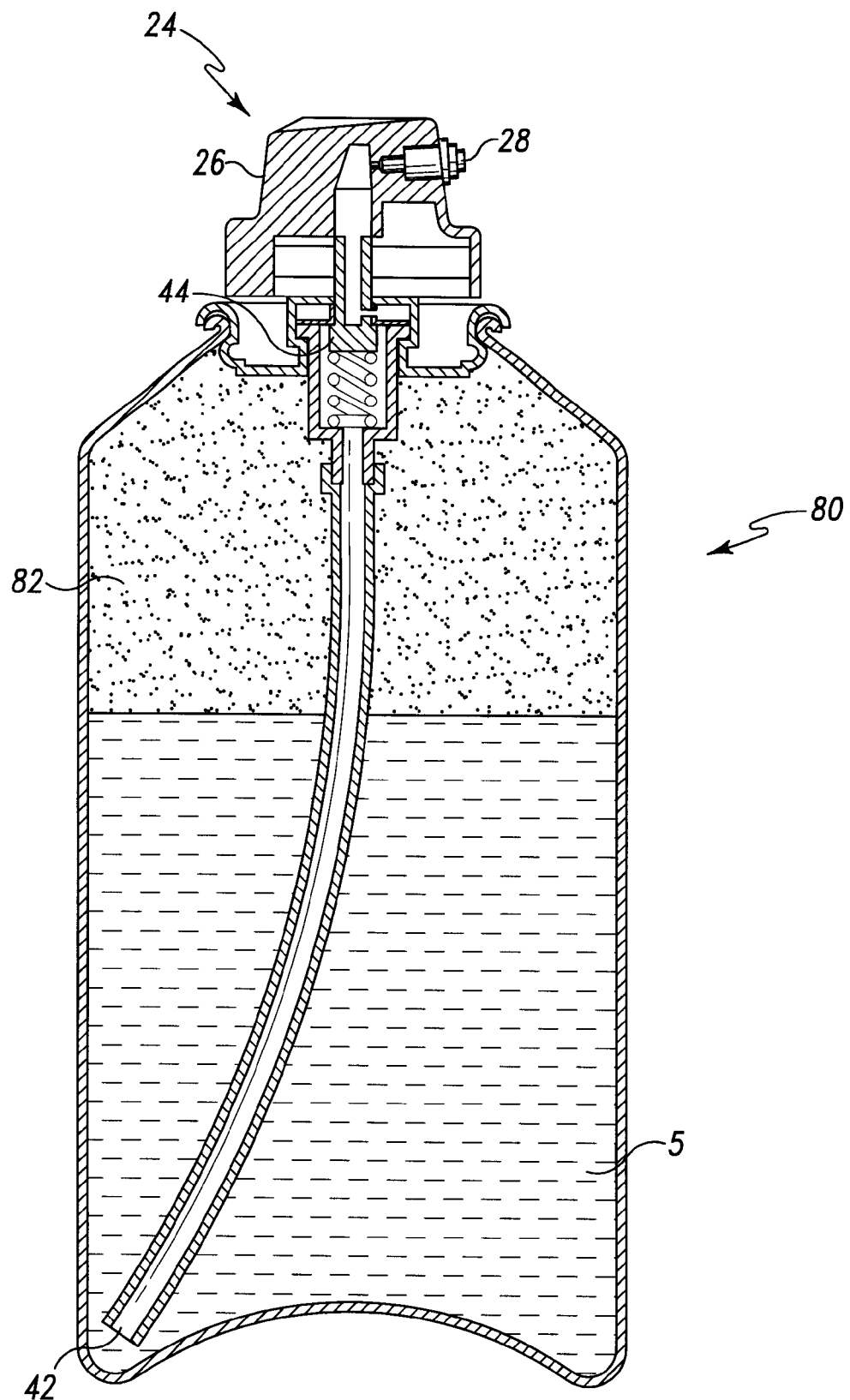
FIG. 6 is a sectional side elevational view of a representative aerosol dispenser in accordance with another embodiment of the invention.

In one excellent embodiment of the invention, a representative example of which is depicted in FIG. 3, the pressure release device is a piston-style dispenser 60, and pressure is maintained on the composition 5 by pressure of a piston 62. The pressure of the piston 62 may be provided by placement of a pressurized gas 64 beneath the piston 62, which placement may be advantageously achieved by introducing gas 64 through a gas charging port 66. Alternatively, pressure on the piston may be achieved by a spring loaded mechanism beneath the piston. Such piston-style dispensers are commercially available, as are a wide variety of designs for actuating the dispensers and for atomizing the composition contained therein. While it is not intended that the invention be limited by the design of the piston-style can, representative examples are set forth in U.S. Pat. No. 4,134,523 to Hansen.

In another excellent embodiment of the invention, representative examples of which are depicted in FIGS. 4 and 5, the pressure release device comprises a bag-in-can-style dispenser 70. The pressurized compartment of such a container is a polymeric bag 72 received inside a rigid can 73. Pressure is maintained on the composition 5 inside the bag 72. In one aspect of the invention, a representative example of which is depicted in FIG. 4, the pressure is maintained upon the composition by a pressurizing gas 74 received in the can 73 and externally to the bag 72. The pressurizing gas 74 may be advantageously placed in the can 73 by introducing gas 74 through a gas charging port 76. In another aspect of the invention, an example of which is depicted in FIG. 5, the bag 72 is an elastic shape-memory bag, and pressure is maintained upon the composition 5 by maintaining the bag in an expanded state. This type of container is commonly referred to as a bladder pack container.

A wide variety of bag-in-can-style containers are commercially available, as are a wide variety of designs for actuating the dispensers and for atomizing the composition contained therein. While it is not intended that the invention be limited by the design of the bag-in-can-style container, representative examples are set forth in U.S. Pat. No. 3,788,521 to Laauwe, U.S. Pat. No. 4,510,734 to Banks et al., and U.S. Pat. No. 5,249,747 to Hanson et al.

Another atomizing spray dispenser that may be used in accordance with the invention, a representative example of which is shown in FIG. 6, is an aerosol device 80. As used herein, the term "aerosol device" is intended to refer to a device that delivers the diaper rash spray treatment composition by entraining the same in a carrier stream comprising an inert pressurized propellant gas 82. When such a device is actuated, the composition is released from the container, entrained in a gaseous stream, atomized, and propelled substantially in a predetermined direction by using energy provided by the pressurized gas. It is understood that the composition and carrier gas may alternately be contained in the container in a pre-mixed form, whereby actuation of the device results in a substantially constant release of the mixture. A wide variety of aerosol containers are commercially available, as are a wide variety of designs for actuating the dispensers and for atomizing the compositions contained therein. While it is not intended that the invention be limited by the design of the aerosol container, representative examples are set forth in U.S. Pat. No. 4,001,391 to Feinstone et al., U.S. Pat. No. 4,187,985 to Goth, U.S. Pat. No. 4,239,407 to Knight, U.S. Pat. No. 4,495,168 to Schmolka, U.S. Pat. No. 5,788,389 to de Laforcade, and U.S. Pat. No. RE030,093 to Burger.

While a wide variety of configurations and styles of atomizing spray dispensers are known in the art, the known prior art does not disclose or suggest the present invention, in which excellent diaper rash treatment compositions are delivered to a skin surface from an atomizing spray dispenser. In view of the above, an excellent system that may be used to achieve efficient treatment of diaper rash is depicted in FIG. 1 and includes a diaper rash treatment composition as described herein and an atomizing spray dispenser 10 for atomizing the composition and delivering the atomized composition to a skin treatment area. The dispenser 10 preferably comprises a container 20, an atomizing spray delivery mechanism 24 affixed to the container 20, and the composition 5 positioned in the container 20. The mechanism preferably comprises an inlet port in fluid communication with the interior of the container for receiving the composition, a device for atomizing the composition, and an outlet port for propelling the atomized composition substantially in a predetermined direction. It is readily understood that, in use, the inlet port must be in contact with the composition.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A method for treating diaper rash, comprising:
    providing a diaper rash treatment system comprising an atomizing spray dispenser and a diaper rash treatment composition; wherein the composition has a viscosity of from about 1 to about 1000 centipoise; wherein the dispenser comprises a container and an atomizing spray delivery mechanism affixed to the container; and wherein the composition is positioned in the container;
    selecting a skin treatment area selected from the group consisting of (i) a skin area normally covered by a diaper, an incontinence pad or an incontinence brief and (ii) an area featuring incontinent dermatitis; and
    passing the composition through the mechanism to atomize the composition and to propel the atomized composition toward the skin-treatment area;
    wherein the composition comprises from about 1 percent to about 40 percent by weight of a solid particulate material, from about 20 percent to about 99 percent by weight of a fluid base material selected from the group consisting of mineral oil, silicone oil, plant-based oil and mixtures thereof, and wherein the composition comprises from 0 percent to about 30 percent water by weight; and leaving said composition on the skin treatment area to form a coating.

2. The method according to claim 1, wherein the solid material comprises particulate zinc oxide.

3. The method according to claim 2, wherein the particulate zinc oxide has an average particle size of from about 0.01 microns to about 100 microns.

4. The method according to claim 2, wherein the particulate zinc oxide has an average particle size of from about 0.01 microns to about 10 microns.

5. The method according to claim 2, wherein the particulate zinc oxide has an average particle size of from about 0.01 microns to about 1 micron.

6. The method according to claim 1, wherein the silicone oil is selected from the group consisting of cyclomethicone and dimethicone.

7. The method according to claim 2, wherein the composition further comprises one or more member selected from the group consisting of talc, lanolin, cod liver oil, petrolatum, paraffin wax and microcrystalline wax.

8. The method according to claim 2, wherein the composition comprises:
    from about 1 percent to about 40 percent by weight zinc oxide;
    from about 20 percent to about 99 percent by weight mineral oil;
    from about 0 percent to about 20 percent by weight silicone oil;
    from about 0 percent to about 12 percent by weight cod liver oil;
    from about 0 percent to about 16 percent by weight lanolin;
    from about 0 percent to about 25 percent by weight petrolatum; and from about 0 percent to about 30 percent by weight water.

9. The method according to claim 2, wherein the composition comprises:
    from about 1 percent to about 40 percent by weight zinc oxide;
    from about 0 percent to about 20 percent by weight mineral oil;
    from about 20 percent to about 99 percent by weight silicone oil;
    from about 0 percent to about 12 percent by weight cod liver oil;
    from about 0 percent to about 16 percent by weight lanolin;
    from about 0 percent to about 25 percent by weight petrolatum; and
    from about 0 percent to about 30 percent by weight water.

10. The method according to claim 2, wherein the composition comprises:
    from about 5 percent to about 25 percent by weight zinc oxide; and
    from about 33 percent to about 80 percent by weight fluid base material.

11. The method according to claim 1, wherein the solid material is selected from the group consisting of talc, calamine and kaolin.

12. The method according to claim 1, wherein the skin treatment area is the diaper area of a patient.

13. A method for treating diaper rash, comprising:
    providing a diaper rash treatment system comprising an atomizing spray dispenser and a diaper rash treatment composition; wherein the composition has a viscosity of from about 1 to about 1000 centipoise; wherein the dispenser comprises a container and an atomizing spray delivery mechanism affixed to the container; and wherein the composition is positioned in the container;

selecting a skin treatment area selected from the group consisting of (i) a skin area normally covered by a diaper, an incontinence pad or an incontinence brief and (ii) an area featuring incontinent dermatitis; and passing the composition through the mechanism to atomize the composition and to propel the atomized composition toward the skin treatment area;

wherein the composition comprises from about 1 percent to about 16 percent by weight lanolin; from about 47 percent to about 97 percent by weight fluid base material selected from the group consisting of mineral oil, silicone oil, plant-based oil and mixtures thereof; from about 1 percent to about 12 percent by weight cod liver oil; and from about 1 percent to about 25 percent by weight petrolatum; and wherein the composition comprises from 0 percent to about 30 percent water by weight; and leaving said composition on the skin treatment area to form a coating.

14. The method according to claim 13, wherein the fluid base material is selected from the group consisting of mineral oil and silicone oil.

15. The method according to claim 13, wherein the composition comprises:

from about 5 percent to about 16 percent by weight lanolin;

from about 57 percent to about 85 percent by weight fluid base material;

from about 5 percent to about 12 percent by weight cod liver oil; and from about 5 percent to about 15 percent by weight petrolatum.

16. The method according to claim 13, wherein the skin treatment area is the diaper area of a patient.

17. A method for treating diaper, rash, comprising:

providing a diaper rash treatment system comprising an atomizing spray dispenser and a diaper rash treatment composition; wherein the composition has a viscosity of from about 1 to about 1000 centipoise; wherein the dispenser comprises a container and an atomizing spray delivery mechanism affixed to the container; and wherein the composition is positioned in the container;

selecting a skin treatment area selected from the group consisting of (i) a skin area normally covered by a diaper, an incontinence pad or an incontinence brief and (ii) an area featuring incontinent dermatitis; and passing the composition through the mechanism to atomize the composition and to propel the atomized composition toward the skin treatment area;

wherein the composition comprises from about 50 percent to about 99 percent by weight of a fluid base material selected from the group consisting of mineral oil, silicone oil, plant-based oil and mixtures thereof and from about 1 percent to about 15 percent by weight of a member selected from the group consisting of calendula, chamomile and comfrey and mixtures thereof; and wherein the composition comprises from 0 percent to about 30 percent water by weight; and leaving said composition on the skin treatment area to form a coating.

18. The method according to claim 17, wherein the fluid base material is a plant-based oil.

19. The method according to claim 17, wherein the fluid base material is selected from the group consisting of almond oil, peanut oil, wheat germ oil, linseed oil, jojoba oil, apricot pit oil, walnut oil, palm nut oil, pistachio nut oil, sesame seed oil, rapeseed oil, cade oil, corn oil, peach pit oil, poppyseed oil, pine oil, castor oil, soybean oil, avocado oil, safflower oil, coconut oil, hazelnut oil, olive oil, grape seed oil, sunflower oil, apricot kernal oil, geranium oil, ricebran oil and mixtures thereof.

20. The method according to claim 17, wherein the composition further comprises one or more member selected from the group consisting of cod liver oil, paraffin wax, microcrystalline wax and bees wax.

21. The method according to claim 17, wherein the skin treatment area is the diaper area of a patient.

22. The method according to claim 1, wherein the composition has a viscosity of from about 20 to about 650 centipoise.

23. The method according to claim 1, wherein the composition has a viscosity of from about 100 to about 600 centipoise.

24. The method according to claim 1, wherein the composition further comprises a member selected from the group consisting of a fragrance, a dye, a preservative, an emollient, an anti-bacterial agent, an anti-fungal agent, talc, calamine, kaolin, lanolin, petrolatum, microcrystalline wax, paraffin wax, bees wax and a mixture thereof.

25. The method according to claim 13, wherein the composition has a viscosity of from about 20 to about 650 centipoise.

26. The method according to claim 13, wherein the composition has a viscosity of from about 100 to about 600 centipoise.

27. The method according to claim 13, wherein the composition further comprises a member selected from the group consisting of a fragrance, a dye, a preservative, an emollient, an anti-bacterial agent, an anti-fungal agent, talc, calamine, kaolin, microcrystalline wax, paraffin wax, bees wax and a mixture thereof.

28. The method according to claim 17, wherein the composition has a viscosity of from about 20 to about 650 centipoise.

29. The method according to claim 17, wherein the composition has a viscosity of from about 100 to about 600 centipoise.

30. The method according to claim 17, wherein the composition further comprises a member selected from the group consisting of a fragrance, a dye, a preservative, an emollient, an anti-bacterial agent, an anti-fungal agent, talc, calamine, kaolin, lanolin, petrolatum, microcrystalline wax, paraffin wax, bees wax and a mixture thereof.

* * * * *